United States Patent
Scott et al.

(10) Patent No.: US 7,094,425 B2
(45) Date of Patent: Aug. 22, 2006

(54) ENTERIC AND COLONIC DELIVERY USING HPMC CAPSULES

(75) Inventors: Robert A. Scott, Sint Niklaas (BE); Ewart T. Cole, Hofstetten (CH)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/836,627

(22) Filed: Apr. 17, 2001

(65) Prior Publication Data

US 2001/0036473 A1 Nov. 1, 2001

Related U.S. Application Data

(63) Continuation of application No. 09/396,225, filed on Sep. 15, 1999, now abandoned.

(60) Provisional application No. 60/102,017, filed on Sep. 28, 1998.

(51) Int. Cl.
*A61K 9/48* (2006.01)

(52) U.S. Cl. ............... 424/451; 424/453; 424/454; 424/463

(58) Field of Classification Search ........... 424/451, 424/453, 454, 457, 458, 459, 461, 462, 463
See application file for complete search history.

(56) References Cited

U.S. PATENT DOCUMENTS

| | | | |
|---|---|---|---|
| 4,138,013 A | 2/1979 | Okajima | 206/528 |
| 5,314,696 A * | 5/1994 | Paulos | 424/453 |

FOREIGN PATENT DOCUMENTS

| | | |
|---|---|---|
| DE | 9414065 | 11/1994 |
| EP | 0754452 | 1/1997 |
| EP | 0754452 A2 * | 1/1997 |
| EP | 0919228 | 6/1999 |
| WO | 95/35100 * | 12/1995 |
| WO | 9535100 | 12/1995 |

* cited by examiner

*Primary Examiner*—Humera N. Sheikh
(74) *Attorney, Agent, or Firm*—Rosemary M. Miano; Evan J. Federman

(57) ABSTRACT

The invention provides a drug delivery system for delivering a drug to either the small intestine (enteric) or the colon comprising a HPMC capsule containing the drug and wherein the HPMC capsule is provided with a suitable coating such that the drug is released from the capsule either in the small intestine or the colon.

28 Claims, 2 Drawing Sheets

RELEASE PROFILE OF ACETAMINOPHEN FROM HPMC CAPSULES COATED WITH VARIOUS QUANTITIES OF EUDRAGIT L30D-50

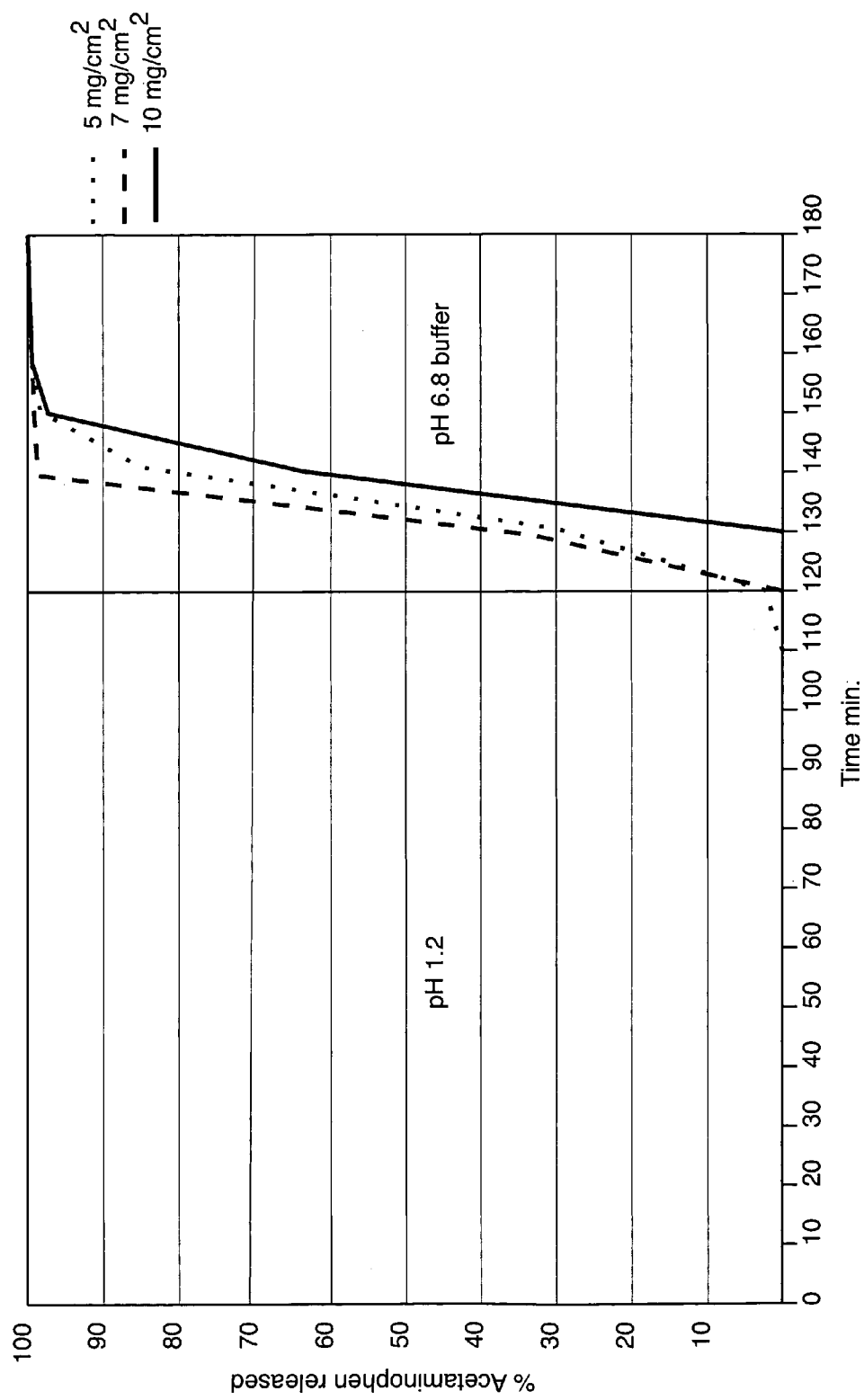

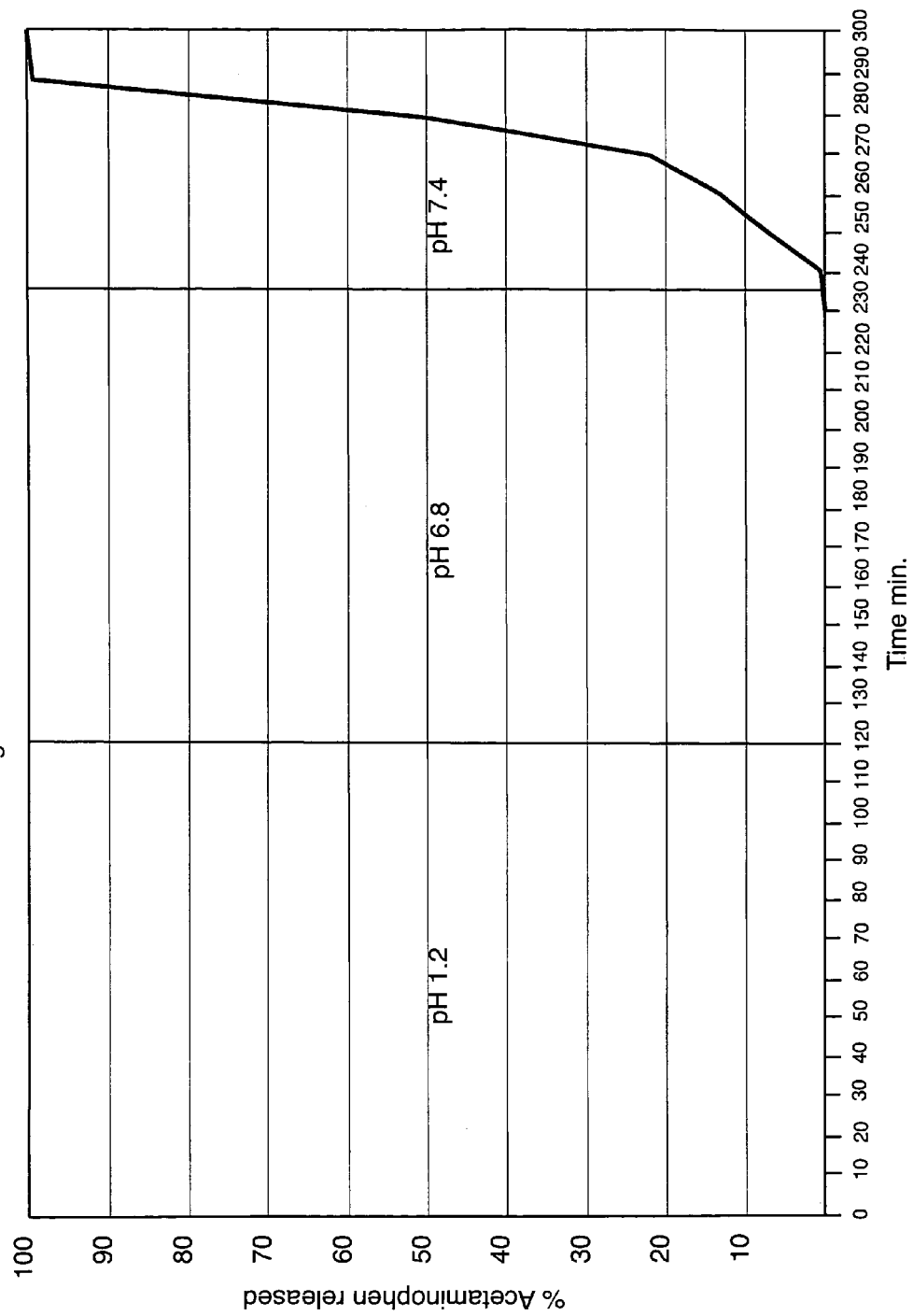

ENTERIC AND COLONIC DELIVERY USING HPMC CAPSULES

This application is a Continuation of Application Ser. No. 09/396,225 filed Sep. 15, 1999, now abandoned, which claims benefit of Provisional Application No. 60/102,017 filed Sep. 28, 1998.

Enteric coated products are designed to remain intact in the stomach but to dissolve and release the active substance in the upper intestine. This type of product is termed a delayed release dosage form.

Most commercially available products in this category are tablets or pellets filled into hard gelatin capsules. Enteric coated preparations are usually used for one or more of the following purposes:

To protect the drug from the destructive action of the enzymes or low pH environment of the stomach.

To prevent or reduce nausea associated with a drug's irritation of gastric mucosa.

To deliver the drug in an undiluted form to its absorption site in the intestine.

The polymers commonly used to achieve enteric properties are polymethacrylates (copolymerisate of methacrylic acid and either methylmethacrylate or ethyl acrylate (EUDRAGIT®), cellulose based polymers e.g. cellulose acetate phthalate (AQUATERIC®) or polyvinyl derivatives e.g. polyvinyl acetate phthalate (COATERIC®).

Colonic products, on the other hand are also designed to remain intact in the stomach but to release the active substance further along the gastrointestinal tract, i.e., in the colon. The site specific delivery of drugs to the colon has implications in a number of therapeutic areas. These include:

The local treatment of colonic diseases such as Crohn's disease, irritable bowel syndrome, ulcerative colitis and colon cancer.

The ability to deliver a drug into the colon which is susceptible to hydrolysis in the G.I. tract. Advances in biotechnology are producing increasing numbers of proteins and peptides. Protecting these labile compounds during their transit through the hostile environment of the upper G.I. tract and delivering them directly to the colon, a site low in host digestive enzymes and of more favourable pH will increase their chance of being absorbed.

The ability to delay systemic absorption in diseases such as asthma, arthritis or inflammation which are affected by circadian rhythmus.

A number of technologies, both marketed and in development, have been described which claim to provide colon specific drug delivery (2–24).

As previously mentioned, site specific delivery into the upper intestine has been achieved for many years by the use of pH-sensitive coatings. By applying a thicker coating and/or raising the threshold pH at which dissolution of the coating begins colon specific delivery using enteric polymers has been achieved. Tablets containing mesalazine and coated with Eudragit® S100, (Roehm GmbH, Darmstadt, Germany) which dissolves above pH 7, are marketed in a number of countries (Asacol®, SmithKline Beecham, UK), Mesalazine tablets coated with Eudragit® L100, (Roehm GmbH, Darmstadt, Germany) which dissolves above pH 6, are also commercially available (Claversal® available from GlaxoSmithKline, Madrid Spain and Salofalk® Dr. Falk Pharma GmbH, Freiburg, Germany).

The majority of the enteric and colon delivery systems are based on tablets or pellets which are filled into conventional hard gelatin capsules.

During the early stages of drug development some new chemical entities (NCE's) present a challenge in testing for efficacy due to instability in gastric fluids or because of irritation in the gastrointestinal tract. In these situations, enteric or colonic coating of an encapsulated drug formulation would enable the efficacy of the drug to be determined without the complications of gastric instability or irritation. The limited amount of drug substance available during the early stage preclude the development of a coated pellet or tablet formulation. Since the coating process is independent of the capsule contents the advantages resulting from the ability to coat a capsule are obvious. Thus the oral pharmacological and/or therapeutic efficacy of the NCE can be determined without resorting to extensive formulation development studies which are expensive, time consuming and, in many instances, impossible at this point in the development of the NCE. Additionally, the capsule provides the possibility to deliver liquid or semi-solid formulations to the small or large intestine.

The most commonly used material for manufacturing capsules is gelatin. Although it is possible to coat hard gelatin capsules the process is at best very sensitive, especially if an aqueous coating system is used, and can lead to shell embrittlement and poor adhesion of the coat to the smooth gelatin surface. A pre-coating can reduce interactions between the gelatin and the enteric polymer but is time consuming and complicated.

Watts (16) has described a colonic drug delivery system based on a starch injection moulded capsule. This system has all the advantages of a capsule described above but suffers from the disadvantage of requiring a specially designed capsule filling and sealing machine, thus narrowing the field of application of the technology.

Surprisingly we have found that the disadvantages of the hard gelatin capsule and the general prejudice associated with coating of this dosage form to achieve enteric or colonic delivery can be significantly reduced by the use of capsules made from hydroxypropylmethyl cellulose. This capsule has the same shape as a conventional hard gelatin capsule and can be filled using standard and widely available capsule filling machines.

The invention therefore provides a drug delivery system for delivering a drug to either the small intestine (enteric) or the colon comprising a HPMC capsule containing the drug and wherein the HPMC capsule is provided with a suitable coating such that the drug is released from the capsule either in the small intestine or the colon.

BRIEF DESCRIPTION OF THE DRAWINGS

FIG. 1 depicts the release profile of acetaminophen from HPMC coated capsules.

FIG. 2 depicts the release profile of acetaminophen front HPMC coated capsules.

In a preferred embodiement of the invention the HPMC capsules are sealed after filling in the overlapping region of capsule body and cap by commonly known sealing techniques like banding or applying a sealing liquid and/or heat to the gap between capsule body and cap. Preferred is a sealing process, in which a sealing liquid which may include a solfvent applied individually and uniformly to the external edge of the gap of a capsule to be sealed to form a liquid ring around the circumference of the capsule, removing excess sealing liquid from the exterior of the capsule and drying the capsule by applying thermal energy from outside. Such a sealing before coating will prevent problems e.g. with non-uniformity of the coating at the gap or development of fissures during storage under stressing conditions, which can lead to an unwated early leaking of the capsule content into the stomach.

Surprisingly it has been found that enteric coated HPMC capsule have superior properties than enteric coated gelatin capsules, especially much higher resistance against acid solutions. In comparative tests 6 from 6 gelatin capsules coated with Eudragit L30D at 10 mg/cm2 opened in a disintegration test after 30 min at pH 1.2, wheras coated HPMC capsules only at 7 mg/cm2 withstood 120 min at pH 1.2.

The composition of the coating should ensure a complete disintegration of the coating in the small intestine or the colon while at the same time minimizing the possibility of the coating disintegrating either in the stomach or passing through the gastrointestinal tract intact.

For release in the small intestine any coating can be used which ensures that the capsule does not disintegrate until it is emptied from the stomach. The coating will usually be one which is pH sensitive and which completely dissolves in the small intestine. Typical coating thicknesses will be in the range 5 to 15 mg polymer per $cm^2$ of capsule surface.

For a capsule of size 1 with a surface area of approx. 4 $cm^2$ this represents a weight gain of 20 mg to 60 mg per capsule (50–150 μm).

Preferred coating materials are those which dissolve at a pH of 5–6. The coatings therefore only begin to dissolve when they have left the stomach and then rapidly disintegrate once the capsule has entered the small intestine. Such a coating can be made from a variety of polymers such as cellulose acetate trimellitiate (CAT), hydroxypropylmethyl cellulose phthalate (HPMCP), polyvinyl acetate phthalate (PVAP), cellulose acetate phthalate (CAP) and shellac.

Especially preferred materials for aqueous film coating are copolymers of methacrylic acid and ethyl acrylate, Eudragit® L30D-55 (Roehm GmbH, Darmstadt, Germany).

For release in the terminal ileum or colon any coating can be used which ensures that the capsule does not disintegrate until it is emptied from the stomach. The coating may be one which is pH-sensitive, redox-sensitive or sensitive to particular enzymes or bacteria, such that the coating only dissolves or finishes dissolving in the colon. Thus the capsules will not release the drug until it is in the terminal ileum or colon.

Typical coating thicknesses will be in the range 5–15 mg polymer per $cm^2$ of capsule surface. For a capsule of size 1 with a surface area of approx. 4 $cm^2$ this represents a weight gain of 20 mg to 60 mg per capsule.

Preferred coating materials are those which dissolve at a pH of 7 or above. The coatings only start to dissolve when they have left the stomach and entered the small intestine. By the time the capsule has reached the terminal ileum or colon the coating will have completely dissolved.

Such a coating can be made from a variety of polymers such as cellulose acetate trimellitiate (CAT) hydroxypropylmethyl cellulose phthalate (HPMCP), polyvinyl acetate phthalate (PVAP), cellulose acetate phthalate (CAP), shellac and copolymers of methacrylic acid and ethyl acrylate. Especially preferred materials for aqueous film coating are copolymers of methacrylic acid and ethyl acrylate to which a monomer of methylacrylate has been added during polymerisation. (Preparation 4110 D as known as Eudragit® FS 30 D from EP-A-704 208 and EP-A-704 207, Roehm GmbH, Darmstadt, Germany). Due to the free carboxylic acid group the polymer dissolves at pH 7 or above making it particularly suitable for delivery into the colon.

Using preparation 4110D a coating thickness of 5–15 mg polymer per square cm of capsule surface is preferred.

The colonic region is rich in microbial anaerobic organisms providing reducing conditions. Thus the coating may suitably comprise a material which is redox-sensitive. Such coatings may comprise azopolymers which can for example consist of a random copolymer of styrene and hydroxyethyl methacrylate, cross-linked with divinylazobenzene synthesized by free radical polymerization, the azopolymer being broken down enzymatically and specifically in the colon or may consist of disulphide polymers.

Other materials providing release in the colon are amylose, for example a coating composition can be prepared by mixing amylose-butan-1-ol complex (glassy amylose) with an aqueous dispersion of Ethocel (Ref. 13) or a coating formulation comprising an inner coating of glassy amylose and an outer coating of cellulose or acrylic polymer material (Ref. 17), calcium pectinate, (Ref. 18) pectin, a polysaccharide which is totally degraded by colonic bacterial enzymes (Ref. 11), chondroitin sulphate (Ref. 19) and resistant starches (Ref. 20), dextran hydrogels (Ref. 12), modified guar gum such as borax modified guar gum (Ref. 21), β-cyclodextrin, saccharide containing polymers, which can include a polymeric construct comprising a synthetic oligosaccharides—containing biopolymer including methacrylic polymers covalently couples to oligosaccharides such as cellobiose, lactalose, raffinose, and stachyose, or saccharide—containing natural polymers including modified mucopolysaccharides such as cross-linked chondroitin sulphate and metal pectin salts, for example calcium pectate (Ref. 22), methacrylate-galactomannan (Ref. 23) and pH sensitive hydrogels (Ref. 24).

The drug which is contained in the capsule may be any pharmaceutically or therapeutically active agent which is desirable to deliver to the small intestine, for example pancreatin and other proteolytic enzymes, diclofenac, naproxen, aspirin, indomethacin, omeprazole, cardiac glycosides, electrolyte preparations with sodium, potassium and magnesium salts as well as calcium and iron preparations, bisacodyl preparations and valproic acid.

Drugs which are desirable to deliver to the colon include drugs for the treatment of colon disease, for example 5-ASA; steroids such as hydrocortisone, budesonide; laxatives; octreotide; cisapride; anticholinergies; calcium channel blockers, 5HT3-antagonists such as ondansetron and peptides such as insulin.

The HPMC capsules of the present invention are cheap, easy to manufacture and can be readily filled on standard capsule filling machines. The coating process is easy to carry out and the adhesion between the film and the HPMC capsule is good. Aqueous coating is possible and the resulting capsule is sufficiently robust which is an advantage over gelatin capsules.

Particularly advantageous for the HPMC capsule is the slower drug release profile in acidic media and the fast release profile at a pH of 5 and above. This can result in lower quantities of polymer coat compared to that required for tablets to achieve the desired release in the small intestine or colon.

EXAMPLES

Example 1

Enteric Capsules

HPMC capsules were filled with a blend comprising (by weight) 85.5% acetaminophen, 8.4% microcrystalline cellulose, 5.8% croscarmellose sodium and 0.3% sterotex.

The mean capsule fill weight was 250 mg.

The capsules were coated with a dispersion, the composition of which is given in Table 1.

TABLE 1

Composition of aqueous Eudragit ® dispersion to coat 1.3 kg HPMC capsules

|  | g | Solids g |
| --- | --- | --- |
| Eudragit L30D-55 | 1509 | 453 |
| Triethyl citrate | 91 | 91 |
| Tween 80 (33%) | 20 | 7 |
| Water | 1130 | — |

The dispersion was sprayed onto the HPMC capsules using an Accela-Cota 10. The temperature of the capsule bed during the coating process was 26–32° C.

The mean amounts of polymer applied was from 5 mg/cm$^2$ to 10 mg/cm$^2$.

The dissolution performance of the capsules was tested using the USP method 2 (rotating paddle at 100 rpm). For the first two hours of the test 0.1N HCl (pH 1.2) was used as the test medium. After two hours the test medium was changed to phosphate buffer pH 6.8. Samples were withdrawn from the dissolution vessel at regular intervals and the concentration of acetaminophen in solution was monitored spectrophotometrically. Results from the dissolution test are presented in FIG. 1. Capsules coated with ≧7 mg/cm$^2$ remained completely intact for a period of two hours in acid and thus were considered to be enteric. After exposure to the pH 6.8 buffer medium, dissolution was rapid and complete thus fulfilling the requirement of an enteric product to deliver the drug in an undiluted form to its absorption site in the small intestine.

Example 2

Colonic Capsules

HPMC capsules were filled with a blend comprising (by weight) 85.5% acetaminophen, 8.4% microcrystalline cellulose, 5.8% croscormellose sodium and 0.3% sterotex.

The mean capsule fill weight was 250 mg.

The capsules were coated with a dispersion, the composition of which is given in Table 2.

TABLE 2

Composition of aqueous methacrylic acid/methyl methacrylate dispersion (preparation 4110D) to coat 1.3 kg HPMC capsules

|  | g | Solids g |
| --- | --- | --- |
| Preparation 4110D | 1207 | 362 |
| Triethyl citrate | 18 | 18 |
| Glceryl monostearate | 11 | 11 |
| Tween 80 (33%) | 13 | 4 |
| Water | 728 | — |

The dispersion was sprayed onto the HPMC capsules using an Accela-Cota 10. The temperature of the capsule bed during the coating process was 26–32° C.

The mean amount of polymer applied was 8 mg/cm$^2$.

The dissolution performance of the capsules was tested using the USP method 2 (rotating paddle at 100 rpm). For the first two hours of the test 0.1 N HCl (pH 1.2) was used as the test medium.

After two hours the test medium was changed to phosphate buffer pH 6.8 for one/two hours and finally to phosphate buffer pH 7.4. Samples were withdrawn from the dissolution vessel at regular intervals and the concentration of acetaminophen in solution was monitored spectrophotometrically. Results from the dissolution test are presented in FIG. 2

The invention claimed is:

1. A drug delivery composition consisting essentially of a coated HPMC capsule capable of containing a drug, wherein the HPMC capsule comprises a single aqueous coating such that the drug is not released from the capsule in the stomach.

2. A drug delivery composition according to claim 1, wherein the HPMC capsule is provided with a coating such that the drug is predominately released from the capsule in the small intestine.

3. A drug delivery composition according to claim 1, wherein the HPMC capsule is provided with a coating such that the drug is predominately released from the capsule in the colon and/or terminal ileum.

4. A drug delivery composition according to claim 2 wherein the coating comprises a material which dissolves at a pH of 5.5 or above.

5. A drug delivery composition according to claim 3 wherein the coating comprises a material which dissolves at a pH 7 or above.

6. A drug delivery composition according to claim 2 wherein the coating comprises cellulose acetate trimellitiate (CAT).

7. A drug delivery composition according to claim 2 wherein the coating comprises hydroxypropylmethyl cellulose phthalate (HPMCP).

8. A drug delivery composition according to claim 2 wherein the coating comprises polyvinyl acetate phthalate (PVAP).

9. A drug delivery composition according to claim 2 wherein the coating comprises shellac.

10. A drug delivery composition according to claim 2 wherein the coating comprises a copolymer of methacrylic acid and methylmethacrylate.

11. A drug delivery composition according to claim 3 wherein the coating composition comprises a material which is redox-sensitive.

12. A drug delivery composition according to claim 3 wherein the coating composition comprises an azopolymer or a disulphide polymer.

13. A drug delivery composition according to claim 3 wherein the coating composition comprises a material which is degraded by enzymes or bacteria present in the colon.

14. A drug delivery composition according to claim 3 wherein the coating composition comprises a copolymer of methacrylic acid and methylmethacrylate to which has been added during polymerisation the monomer methyl acrylate.

15. A drug delivery composition according to claim 3 wherein the coating composition comprises a cellulose ester.

16. A drug delivery composition according to claim 3 wherein the coating composition comprises polyvinyl acetate phthalate.

17. A drug delivery composition according to claim 2 wherein the coating is applied in the range of 5–15 mg per cm² of capsule surface.

18. A drug delivery composition according to claim 3 wherein the coating is applied in the range 5–20 mg per cm² of capsule surface.

19. A drug delivery composition according to claim 2 wherein the drug is one which is effective in the small intestine.

20. A drug delivery composition according to claim 1 wherein the drug is one which acts locally in the colon.

21. A drug delivery composition according to claim 1 wherein the coating is applied separately to empty HPMC capsule body and cap.

22. A drug delivery composition according to claim 1 wherein two equal HPMC capsule halves are filled with a caplet.

23. A drug delivery composition according to claim 22 wherein the coating is applied separately to equal empty HPMC capsule halves.

24. A drug delivery composition according to claim 22 wherein one half is coated with an insoluble polymer and the other half is enteric or colonic coated.

25. A drug delivery composition according to claim 1 wherein the HPMC capsule is coated with a film which is non-dissolving at pH<3 to 4 and dissolving at pH>5.5.

26. A drug delivery composition according to claim 1 wherein the HPMC content of the capsule shell is in the range of from 10 to 90% by weight.

27. A drug delivery composition according to claim 1 wherein stomach resistant coating is applied to HPMC capsules having a sealing on the gap between capsule body and cap.

28. A drug delivery composition consisting essentially of an HPMC capsule capable of containing a drug, wherein: (a) drug is not released from the capsule in the stomach; (b) one half of the capsule is enteric coated and the other half is colonic coated; (c) the enteric coating is at least one member selected from the group consisting of cellulose acetate trimellitiate, hydroxypropylmethyl cellulose phthalate, polyvinyl acetate phthalate, shellac, and a copolymer of methacrylic acid and ethyl acrylate: and (d) the colonic coating is a member selected from the group consisting of azopolymers, disulphide polymers and amylose.

* * * * *